United States Patent [19]

Moretti

[11] 4,076,373
[45] Feb. 28, 1978

[54] METHOD OF AND MEANS FOR SHIELDING THE LENS OF A FACE MASK

[75] Inventor: Anthony L. Moretti, San Rafael, Calif.

[73] Assignee: E. D. Bullard Company, Sausalito, Calif.

[21] Appl. No.: 665,691

[22] Filed: Mar. 10, 1976

[51] Int. Cl.² .......................... G02B 7/00; G02C 3/02
[52] U.S. Cl. ...................................... 350/61; 350/65; 350/320; 2/434
[58] Field of Search .................... 350/61, 65, 316, 320; 351/47; 2/434, 9, 8

[56] References Cited
U.S. PATENT DOCUMENTS 3,945,044  3/1976  McGee et al. ...................... 2/14 H Primary Examiner—Jon W. Henry
Attorney, Agent, or Firm—Phillips, Moore, Weissenberger, Lempio & Majestic

[57] ABSTRACT

Shielding of the protective lens of a face mask by forming and mounting a stack of thin sheets of transparent or translucent material on the exterior surface of the protective lens is disclosed. According to this invention, the thin sheets of the stack are removably mounted with respect to each other and with respect to the lens and each sheet is provided with an elongated flexible tab adapted to be folded over and interposed between such sheet and an adjacent sheet in the stack with the tab on only the top sheet projecting free to facilitate removal of such top sheet from the stack without unintentional removal of other sheets of the stack.

11 Claims, 5 Drawing Figures

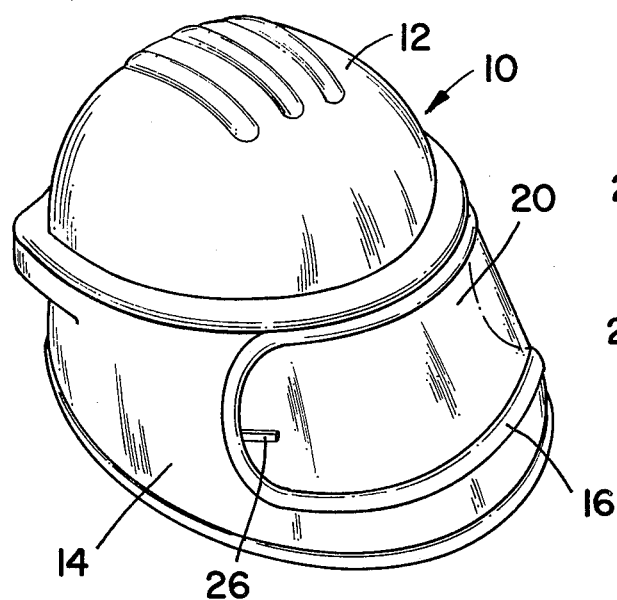
FIG _ 1
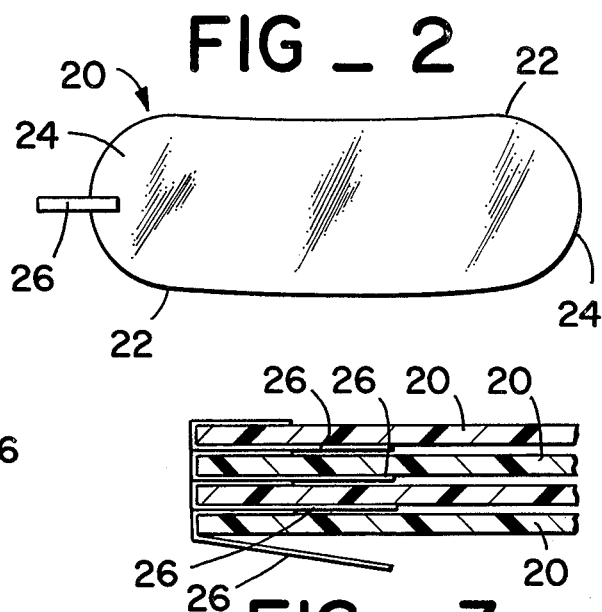
FIG _ 2
FIG _ 3
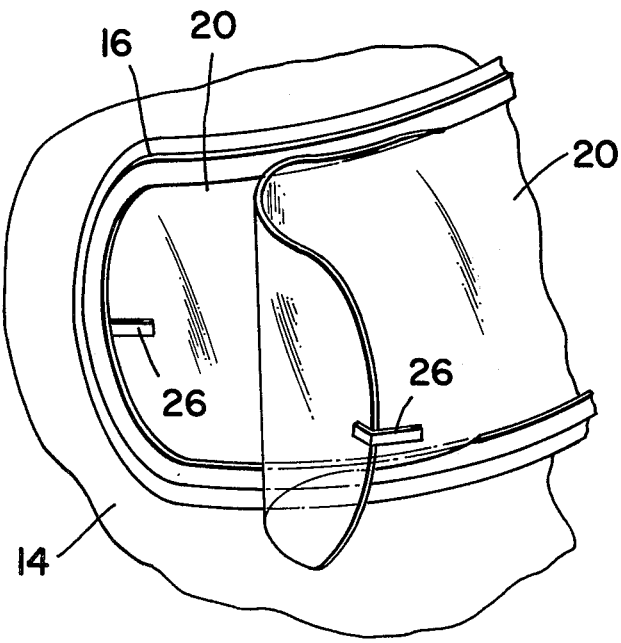
FIG _ 5
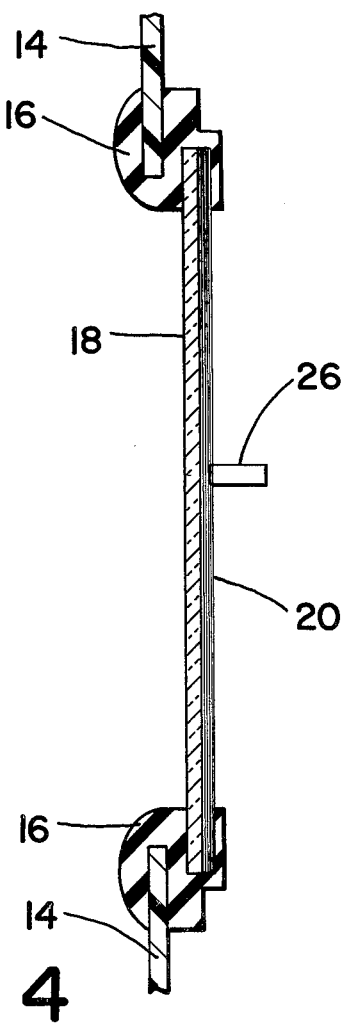
FIG _ 4

METHOD OF AND MEANS FOR SHIELDING THE LENS OF A FACE MASK

BACKGROUND OF THE INVENTION

The invention relates to the shielding of a protective lens and more particularly to the shielding of the lens of a protective face mask against abrasion, pitting, burning and the deposition of opaque material thereon.

It is common for workers to be required to wear protective gear such as helmets including a protective transparent or translucent face mask in addition to move conventional gear such as heavy gloves when performing jobs that may result in excessive heat, injurious light or flying sparks, particles and heavier objects. The transparent or translucent members used in such face masks must be made of materials strong enough and with a thickness dimension large enough to withstand heavy impacts without breaking or giving way. In some cases, such members must be capable of filtering out undesired portions of incident light.

In use, such transparent or translucent members are exposed to forces which tend to scratch or scrape the exterior surface thereof as well as to localized pitting or burning and the deposition of opaque materials thereon. In any event, after use over a period of time, the optical quality of such transparent or translucent members will tend to be impaired to an extent sufficient to produce a safety hazard.

It has been proposed in the prior art to mount the transparent or translucent members on the face mask or helmet structure in such a way as to facilitate removal and replacement of such members (see for example U.S. Pat. No. 2,186,817 issued to Fredrick M. Bowers on Jan. 9, 1940). However, the transparent or translucent members are not inexpensive and they tend to require appropriate storage in quantity other than at the job site. Furthermore, it is necessary to interrupt the job in progress and remove the helmet or face mask from use in order to replace the transparent or translucent member thereof. The end result is that such members are not replaced as soon as they should be and they can introduce a safety hazard due to impaired optical quality which is often as great as the safety hazard they are intended to overcome.

It is an object of this invention to provide a method of and means for shielding the exterior surface of the transparent or translucent members of a face mask structure against abrasion, pitting, burning and the deposition of opaque materials thereon.

It is another object of this invention to provide such a method and means which is simple and inexpensive.

It is a further object of this invention to provide such a method and means which will enable the optical qualities of the face mask to be maintained without interruption of a job in progress or removal of the face mask from service.

It has been proposed in the prior art to provide a lens cover in the nature of a thin sheet or film that can be easily and quickly stuck to the lens and which can likewise be easily and quickly removed. See for example U.S. Pat. No. 2,511,329 issued to Edward Craig on June 13, 1950, in which it is further proposed that the thin sheets be provided with an adhesive on one side thereof and arranged in a pack for carrying or handling and that the sheets can be removed from the pack and applied to the lens one at a time.

However, such sheets are difficult to separate from the pack one at a time, particularly while wearing working gloves. Furthermore, the pack is likely to be lost or mislaid and may not be available at the work site when needed. Finally, the presence of the adhesive across the surface of the lens cover tends to degrade the optical quality thereof and introduce the possibility that foreign matter will adhere thereto and further degrade optical quality.

Thus, it is yet another object of this invention to provide for the shielding of the exterior surface of the transparent member of a face mask by mounting a stack of thin flexible sheets of transparent or translucent material thereagainst for removal therefrom one at a time.

It is a still further object of this invention to provide a thin flexible sheet of transparent or translucent material which is particularly adapted for individual removal from a stack thereof using gloved hands.

It is yet a further object of this invention to provide such a thin flexible sheet which is particularly adapted to provide a visible indication of the fact that a second one thereof is in stacked relation thereto without detracting from the ease of individual removal thereof.

SUMMARY OF THE INVENTION

Briefly, according to the teaching of this invention, the exterior surface of the protective lens of the face mask is shielded against abrasion, pitting, burning and the deposition of opaque material thereon by a plurality of thin flexible sheets of a material which is at least translucent. Such sheets have common length and width dimensions large enough to cover the usable optical area of the exterior surface of the protective lens and each of the plurality of sheets has an elongated flexible tab projecting from the edge thereof. The plurality of thin flexible sheets are arranged in a mutually aligned stack having a top and a bottom with the tab of each sheet bent to extend along the surface thereof which faces the top of the stack and with the tab of each sheet except the sheet at the top of the stack received between such sheet and an adjacent sheet. The stack of the plurality of sheets is removably mounted against the exterior surface of the protective lens only at a limited area along the edges thereof. Thus the top sheet of the stack may be individually removed from the stack and protective lens by grasping the elongated flexible tab of such top sheet and peeling such top sheet away from the stack and protective lens.

BRIEF DESCRIPTION OF THE DRAWING

Referring to the single sheet of drawing,

FIG. 1 is a perspective view of a helmet having a face mask with a stack of flexible sheets mounted against the protective lens of the face mask in accordance with one embodiment of the teaching of this invention;

FIG. 2 is a front view of a thin flexible sheet as used in the embodiment of this invention shown in FIG. 1;

FIG. 3 is an enlarged fragmentary cross-sectional view of a stack of the thin flexible sheets taken at one end thereof in order to show the interposition of the flexible tabs between adjacent sheets in such stack;

FIG. 4 is an enlarged cross-sectional view taken along lines 4—4 of FIG. 1 and showing a stack of thin flexible sheets as mounted against the exterior surface of the protective lens of the embodiment of the invention shown in FIG. 1; and FIG. 5 is an enlarged fragmentary perspective view of the embodiment of this invention of FIG. 1 showing the top flexible sheet in the process of being removed from the stack of thin flexible sheets, the thickness of the flexible sheet being exaggerated for clarity of illustration.

DETAILED DESCRIPTION OF PREFERRED EMBODIMENTS

Referring to FIG. 1, the application of this invention to a helmet 10 comprising a hat portion 12 for protecting the head of the wearer and a face portion 14 for protecting the face of the wearer is shown. The face mask portion 14 of the helmet 10 is provided with an enlarged aperture opposite the eyes and face of the wearer. According to this embodiment of the invention the aperture is provided with a resilient frame or bezel 16 for mounting a transparent or translucent protective lens which closes such aperture in the face mask 14.

As best shown in FIG. 4, the protective lens 18 has a substantial thickness and transverse dimensions larger than the aperture in the face mask 14. The frame 16 is adapted to support the lens 18 exteriorly of the face mask 14 so that the wearer will be protected against impacts from outside the helmet 10 on the protective lens 18 as well as the face mask 14 and hat portion 12 of the helmet 10. Such impacts on the protective lens 18 will tend to force it against the portions of the face mask 14 which it overlaps at its outer periphery.

The thickness of the protective lens 18 and the material of which it is made must provide sufficient strength to withstand heavy impact without breaking, bending or otherwise giving way a sufficient amount to allow injury to the wearer. In addition, it is often necessary that the protective lens 18 be tinted or colored or otherwise adapted to filter out certain wavelengths of the light incident thereon, or a certain amount of the total light incident thereon, in order to protect the eyes of the wearer in use. Thus, the protective lens 18 is not inexpensive.

It has been found that the optical quality of the protective lens 18 will tend to be impaired after a period of use. Such impairment may result from the abrasion of the exterior surface of the protective lens 18 by impact of objects which scratch or scrape such exterior surface. The optical quality of the protective lens 18 may also be reduced due to the pitting or burning of the exterior surface by small, high velocity particles of material as encountered in sandblasting or the impingement of small, high temperature particles thereon as encountered in welding operations. Finally, the optical quality of the protective lens may be impaired by deposition of opaque materials on the exterior surface thereof as, for example, when spray painting operations are being conducted in the vicinity of the wearer.

In any event, it often becomes necessary to replace the protective lens 18 after an undefined period of use due to the degradation of the optical quality thereof as described above. However, in order to replace the protective lens 18, it is necessary that a new protective lens be available and that the job in progress be interrupted and the helmet taken out of service long enough to allow the old protective lens 18 to be removed and the new protective lens to be inserted. Since such replacement operation is inconvenient and requires the interruption of a job in progress, it is common for a particular protective lens 18 to remain in use even after the optical quality thereof has been seriously degraded. Such continued use of a protective lens having poor optical quality introduces a safety hazard that can be equal to or greater than the safety hazard it is intended to protect against.

According to the teaching of this invention, a plurality of thin, flexible, translucent or transparent sheets 20, as shown in FIG. 2, are arranged in a stack which is removably mounted against the exterior surface of the protective lens 18 for removal therefrom, one at a time. According to the embodiment of this invention shown in the drawing, the thin flexible sheets 20 have the same dimensions as the protective lens 18 except that they are much thinner and may be made of an inexpensive material since they need not have a great deal of structural strength. The thin flexible sheets 20 must, of course, be translucent and may be made of a colored or tinted material although they are preferably made of transparent material.

According to this embodiment of the invention, the thin flexible sheets are generally rectangular and all have common side 22 and end 24 dimensions. An elongated, flexible tab 26 projects from a central portion of one end 24 of each of the flexible sheets 20 to facilitate the individual removal of each sheet from a stack of such sheets. According to the embodiment of this invention shown in the drawing, the flexible tab 26 may be made separately from the sheet 20 and have one end affixed thereto with the other end projecting freely from the sheet. However, it would also be possible for the flexible tab 26 to be formed integrally with the sheet 20.

In any event, referring to FIG. 3, a stack of mutually aligned thin flexible sheets 20 is formed by bending the elongated tabs 26 so that the tab 26 of each sheet 20 lies along the surface of such sheet which faces the top of the stack. Thus, according to the teaching of this invention, the tab 26 of each sheet 20 of the stack is interposed between such sheet and the next adjacent sheet of the stack except for the topmost sheet of the stack in which case the flexible tab 26 tends to stand free of the top surface of the sheet to which it is attached.

According to the teaching of this invention, means are provided for mounting the stack of thin flexible sheets 20 against the exterior surface of the protective lens 18 at a peripheral edge portion only of such stack. Thus, in the preferred embodiment of this invention as best shown in FIG. 4, the resilient frame or bezel 16 is adapted to receive a stack comprising a small number of the thin flexible sheets 20 together with the protective lens 18. As best shown in FIG. 5, the topmost one and each succeeding one of the thin flexible sheets 20 in the stack received and held against the exterior surface of the lens 18 by the frame 16, may be peeled away by grasping the elongated tab 26 thereof. According to this embodiment, the elongated tab is provided at an end of the thin flexible sheet in order to reduce the force required for removal of such sheet from mounting engagement with the frame 16.

As best shown in FIGS. 1 and 5, the elongated tabs 26 project into the aperture in the face mask 14 and if made of a tinted, colored or opaque material, they will enable the wearer to determine whether or not there are any thin flexible sheets 20 present on the exterior surface of the protective lens 18 to shield it from damage. Since the elongated tab 26 of the top sheet 20 of a stack of sheets in engagement with the exterior surface of the protective lens 18 will tend to stand free, it can be easily grasped even where the wearer is wearing heavy work gloves and thus the removal of such sheet will be facilitated.

It is believed that those skilled in the art will make obvious modifications in the teaching of this invention for use in specific circumstances, some of which have been suggested hereinabove. It would, of course, be possible to mount the thin flexible sheets 20 to each other in a stack and the stack to the exterior of a protective lens 18 by means of an adhesive. However, according to the teaching of this invention, such adhesive must be present at an edge portion only of the thin transparent sheets in order to avoid any possible optical impairment of the optically active area due to the presence of the adhesive or to foreign matter which might tend to adhere to the adhesive. Furthermore, according to this invention, the thin transparent sheets must be removably mounted against the exterior surface of the protective lens by means which is active about substantially the entire periphery of the sheets, whether it be a resilient means or an adhesive means, in order to prevent small particles of sand, rock or other materials from entering between the sheets of the stack and impairing the optical quality thereof. This is particularly important when the helmet is worn in performing sandblasing operations, for example. Although a face mask having a generally rectangular lens and generally rectangular thin transparent sheets are shown in the drawing, this invention is also applicable where one or both have a generally circular configuration. The elongated tabs 26 should have a sufficient length to facilitate the removal of a sheet from the stack while wearing heavy gloves and to provide an easily discernable optical indication of the presence of one or more thin sheets on the exterior surface of the lens 18.

What is claimed is:

1. Means for shielding the exterior surface of the protective lens of a face mask comprising:
   a. a plurality of thin flexible sheets of material each of which is capable of transmitting at least some light with each said sheet having given length and width dimensions large enough to cover the usable optical area of said exterior surface of said protective lens and with each said sheet having an elongated flexible tab projecting from the edge thereof, said plurality of said thin flexible sheets having said length and width dimensions thereof arranged in a mutually aligned stack having its bottom sheet against said exterior surface of said protective lens with said tab of each said sheet bent to extend generally along the top surface thereof and with said tab of each said sheet except the top sheet of said stack received between such sheet and the bottom surface of the sheet adjacent thereto in said stack; and
   b. means removably mounting said stack of said plurality of said thin flexible sheets against said exterior surface of said protective lens, said means being active at a limited area only along substantially the entire periphery of the edge of said stack of said plurality of thin flexible sheets.

2. Means for shielding the exterior surface of the protective lens of a face mask as claimed in claim 1 wherein each said elongated flexible tab is made of a different material from said material of said sheets and is affixed at one end to the bottom surface of said sheets.

3. Means for shielding the exterior surface of the protective lens of a face mask as claimed in claim 1 wherein the length of each said elongated tab and the material of which it is made renders said tab visible through the material of said sheets.

4. Means for shielding the exterior surface of the protective lens of a face mask as claimed in claim 1 wherein said means removably mounting said stack of said sheets against said lens comprises a frame of resilient material overlapping a limited area only along the sides and ends of said stack and adapted to compressively urge said stack toward said lens.

5. Means as claimed in claim 1 wherein said thin flexible sheet is generally rectangular with said length dimension of the sides thereof greater than said width dimension of the ends thereof and with said elongated flexible tab projecting from an end thereof.

6. The method of shielding the exterior surface of the protective lens of a face mask comprising the steps of:
   a. forming a plurality of thin flexible sheets of material which is capable of transmitting at least some light with each said sheet having given length and width dimensions large enough to cover a usable optical area of the exterior surface of said protective lens and with each said sheet having an elongated flexible tab projecting from the edge thereof;
   b. bending said elongated tab of each said sheet to extend along one surface thereof;
   c. arranging said plurality of sheets in a mutually aligned stack having a top and a bottom with said one surface of each sheet facing said top of said stack and the other surface of each sheet facing said bottom of said stack and with said tab of each said sheet except the sheet at the top of said stack received between adjacent sheets; and
   d. removably mounting said stack of said thin flexible sheets against said exterior surface of said protective lens by means acting at a limited area only along substantially the entire periphery of the edge thereof with said other surface of the sheet at the bottom of said stack positioned against said exterior surface of said protective lens whereby the sheets of said stack may be removed one at a time from said protective lens by grasping said elongated flexible tab of the sheet at the top of said stack and peeling said sheet away from said protective lens.

7. The method of claim 6 wherein said step of forming each said thin flexible sheet having an elongated flexible tab projecting from the edge thereof further comprises the steps of forming said elongated tab separately from said sheet and affixing one end of said tab to said other surface of said sheet.

8. The method of claim 6 wherein said plurality of sheets in said stack are removably mounted against said exterior surface of said protective lens at a limited area only along the edge thereof by exerting resilient compressive force on said stack at said limited area along substantially the entire periphery thereof.

9. The method of claim 6 wherein said step of forming each said thin flexible sheet further comprises the step of making the length and width dimensions thereof substantially equal to the length and width dimensions of said protective lens.

10. The method of claim 7 wherein said step of forming said elongated tab separately from said sheets further comprises the step of forming said elongated tab of a different material from said sheets which material is visible when viewed through the material of said sheet.

11. The method of claim 1 wherein the step of forming each said thin flexible sheet includes the further step of making said sheet generally rectangular with said given length dimension of the sides thereof greater than said given width dimension of the ends thereof and said elongated flexible tab projecting from one end thereof.

* * * * *